(12) United States Patent
Jones, III et al.

(10) Patent No.: US 7,630,847 B2
(45) Date of Patent: Dec. 8, 2009

(54) METHODS FOR PREDICTING DIMENSIONAL STABILITY OF A WOOD PRODUCT BASED ON DIFFERENTIAL CHARACTERISTICS

(75) Inventors: John E Jones, III, Seattle, WA (US); Mark A Stanish, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 0 days.

(21) Appl. No.: 11/690,935

(22) Filed: Mar. 26, 2007

(65) Prior Publication Data

US 2008/0243270 A1    Oct. 2, 2008

(51) Int. Cl.
    *G06F 3/00* (2006.01)
(52) U.S. Cl. ............................... 702/81; 702/82; 702/84; 702/179
(58) Field of Classification Search ............... 702/155, 702/170, 181, 186, 189, 190; 73/597; 324/637; 144/356
    See application file for complete search history.

(56) References Cited

U.S. PATENT DOCUMENTS

| | | | |
|---|---|---|---|
| 3,936,665 A * | 2/1976 | Donoghue | ............... 700/129 |
| 4,497,027 A * | 1/1985 | McGuire et al. | ............ 700/127 |
| 6,305,224 B1 * | 10/2001 | Stanish et al. | ................. 73/597 |
| 6,598,477 B2 | 7/2003 | Floyd | |
| 6,996,497 B2 | 2/2006 | Floyd et al. | |
| 7,017,413 B2 * | 3/2006 | Floyd et al. | ................... 73/597 |
| 7,286,956 B2 * | 10/2007 | Floyd et al. | ................ 702/159 |
| 7,324,904 B2 | 1/2008 | Floyd et al. | |

OTHER PUBLICATIONS

Remond et al "The effect of temperature and moisture content on the mechanical behaviour of wood: a comprehensive model applied to drying and bending" Euro J of Mech, vol. 23 No. 3, pp. 558-572. A, Solids, Gauthier-Villars, Paris Feb. 2007.

* cited by examiner

*Primary Examiner*—Eliseo Ramos Feliciano
*Assistant Examiner*—Felix E Suarez
(74) *Attorney, Agent, or Firm*—Rachael Vaughn

(57) ABSTRACT

Methods are provided for predicting warp of a wood product given its differential characteristics, such as, for example, curvature. The methods may involve measuring at least one original warp profile for each of one or more first wood products; measuring one or more inputs on the one or more first wood products; converting the warp profile, for each of the one or more first wood products, into a differential characteristic profile; developing a prediction algorithm based on the one or more inputs and the differential characteristic profile; measuring one or more inputs of the given wood product; inputting the one or more inputs of the given wood product into the prediction algorithm; and determining a differential characteristic profile for the given wood product based on the prediction algorithm.

13 Claims, 4 Drawing Sheets

METHODS FOR PREDICTING DIMENSIONAL STABILITY OF A WOOD PRODUCT BASED ON DIFFERENTIAL CHARACTERISTICS

FIELD OF THE INVENTION

This invention relates generally to methods for describing the shape of a lumber-warp-profile in terms of differential characteristics, such as, for example, curvature, and predicting the warp of a given wood product.

BACKGROUND OF THE INVENTION

Wood products, such as logs, boards, other lumber products, or the like, can be graded or classified into qualitative groups by the amount of warp potential, or dimensional stability, in the product. Crook, bow, twist, and cup are examples of warp and are illustrated in FIG. 1. The groups are used to qualitatively represent the warp state at a specified ambient condition or the degree of warp instability of a wood product. The qualitative groups are typically ordinal in nature, though nominal categories may also be used.

The degree of warp depends on several known factors, such as density, modulus of elasticity (hereinafter referred to as "MOE"), moisture content variation, pith location, compression wood, grain angle and others. Many of these factors can be quantitatively or qualitatively evaluated with different types of sensors. For example, MOE can be estimated from the propagation of sound through wood, and specific gravity can be estimated from the capacitance of wood. A different type of sensor group or system may be utilized for detecting each of these properties.

During the three year period from 1995 to 1998, solid sawn softwood lumber usage in wall framing, floor framing and roof framing dropped by 9.9%, 17.2% and 11% respectively in the United States (Eastin et al., 2001)[1]. In this survey of nearly 300 builders, lumber straightness was rated the most important factor affecting buying decisions; yet of all the quality attributes surveyed, dissatisfaction with straightness was highest. It is generally recognized that softwood lumber will continue to lose market share unless the industry improves the in-service warp stability of its product.

[1]Eastin, I. L., Shook, S. R., Fleishman, S. J., Material substitution in the U.S. residential construction industry, 1994 versus 1988, *Forest Products Journal*, Vol. 51, No. 9, 31-37.

In the United States, most softwood dimension lumber is visually graded for a variety of attributes that affect its appearance and structural properties. These attributes include knots, wane, dimension (thickness, width, and length), decay, splits and checks, slope-of-grain, and straightness (warp). Strict quality control practices overseen by third party grading agencies are in place to ensure that all lumber is "on-grade" at the point the grade is assigned. Unfortunately, the straightness and dimension of a piece are not static and can change after the piece is graded. Additional warp and size change can develop after the piece is in the distribution channel or after it is put into service. Typical moisture content of fresh kiln dried lumber averages 15% but ranges from 6% to 19%. This lumber will eventually equilibrate to a moisture ranging from 3% to 19% depending on time of year, geography and whether the application is interior or exterior (Wood Handbook)[2]. This moisture change results in changes in both dimension and warp properties. Any piece of lumber is prone to develop additional "in-service" warp if a) its shrinkage properties are not uniform and it changes moisture or b) its moisture content is not uniform at the point the original grade was assigned. Neither of these conditions is detectable with traditional visual grading methods. Customers of wood products seek stability in both dimension and warp properties.

[2]Wood Handbook. General Technical Report 113(1999) Department of Agriculture. Forest Service. Forest Products Laboratory The wood handbook[2] provides guidelines for assessing the width and thickness stability of solid sawn lumber. Average thickness and width shrinkage is governed by grain orientation as well as radial and tangential shrinkage properties. These average radial and tangential shrinkage values vary by species and are reduced if heartwood is present. Although these methods can be used to estimate the average thickness and width shrinkage behaviour of a species, methods for precise quantification do not exist. There are even fewer design tools for estimating length shrinkage.

Today the patterns of equilibrium moisture and shrinkage coefficients within a full size lumber product can be accurately measured only in a laboratory environment. The laboratory technique involves cutting the piece of lumber into small "coupons" and measuring the moisture content and shrinkage coefficients using ASTM standards D-4492 and D-143, respectively. Although much is known about equilibrium moisture and shrinkage behaviour of wood, there are as yet no comprehensive theoretical models and no methods of monitoring these properties in a real time production environment.

Unfortunately, none of the individual methods described above are accurate enough to give adequate estimates of the dimensional stability of a single piece of lumber. Thus, a need exists for methods for describing the shape of a lumber-warp-profile in terms of differential characteristics.

BRIEF DESCRIPTION OF THE DRAWINGS

The embodiments of the present invention are described in detail below with reference to the following drawings.

DETAILED DESCRIPTION OF THE INVENTION

The present invention generally relates to methods for predicting warp of a wood product given its differential profile characteristics, such as, for example, first derivative, second derivative, curvature, or the like. The warp may be cook, bow or twist. The methods may involve measuring at least one original warp profile for each of one or more first wood products; measuring one or more inputs on the one or more first wood products; converting the warp profile, for each of the one or more first wood products, into a differential characteristic profile; developing a prediction algorithm based on the one or more inputs and the differential characteristic profile; measuring one or more inputs of the given wood product; inputting the one or more inputs of the given wood product into the prediction algorithm; and determining a differential characteristic profile for the given wood product based on the prediction algorithm.

Figure 1:
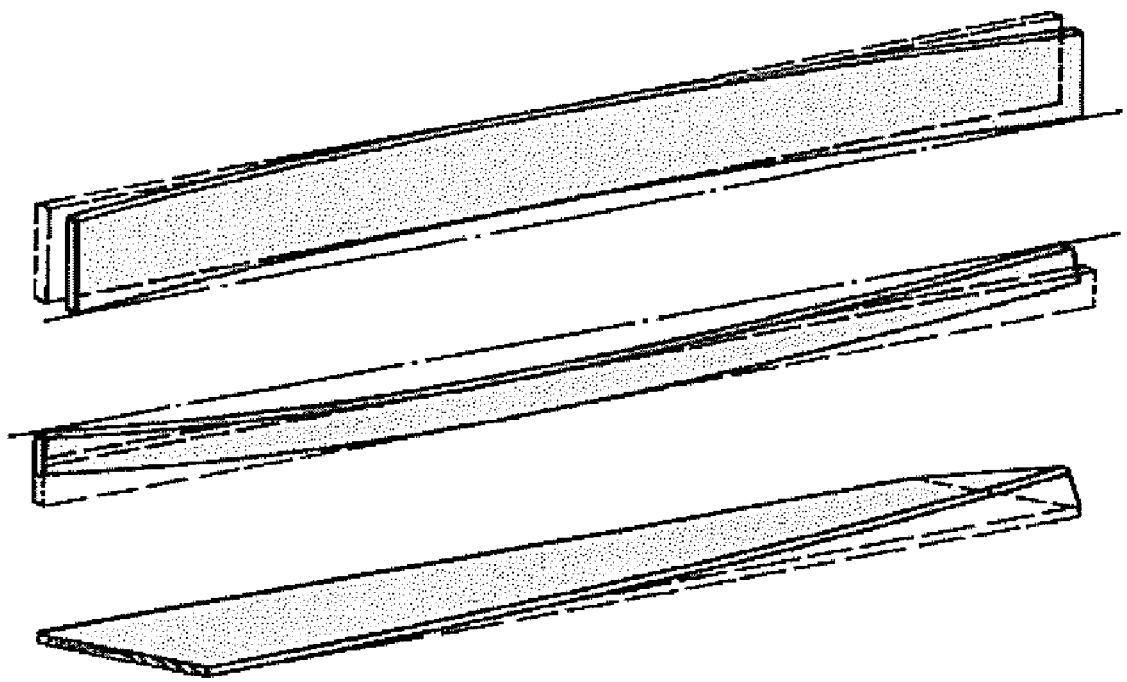
FIG. 1 provides examples of crook, bow, twist, and cup in a wood product.
Figure 3:
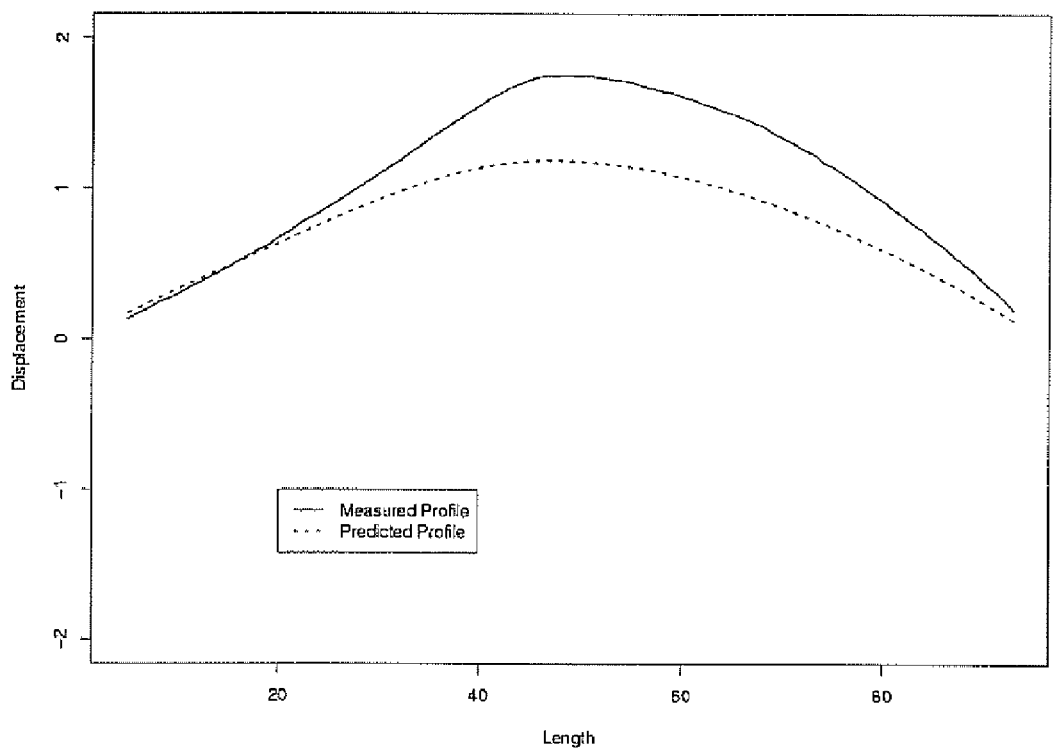
FIG. 3 is a plot of a predicted profile in an embodiment of the present invention.

FIG. 1 shows examples of crook, bow and twist of a lumber product. The warp profile for bow measures the deviation from a flat-wise (wide-face) straight line drawn from end to end, down the length of the piece of lumber. For example, the solid line in FIG. 3 shows a warp profile. The warp profile for crook measures the deviation from an edge-wise (narrow-face) straight line drawn from end to end, down the length of the piece of lumber. A twist profile measures the flat-wise deviation of the free edge of a piece of lumber, down the length of the piece when three corners are held at fixed reference positions.

In an embodiment, a first step may be creating an algorithm. This may be accomplished by collecting a sample of wood, such as one or more boards or other wood products taken from a log. Measurements on the wood may be taken using one or more sensor groups or methods. These measurements may be conducted in a lab, or on-line during production. The warp of the boards may be measured along with the current moisture content. These measurements could also be conducted in a lab, or on-line during production. Next, the warp profile is converted to a differential characteristic profile. It should be noted that since the warp profile will not likely follow a known functional form and the differential characteristic profile may have to be estimated. There are many numeric and statistical methods for this estimation.

The measured warp profile can be considered a function of x, where x is the distance down the length of a lumber product. The differential characteristic profile represents a differential of the warp profile in x, or a function of differential profiles in x, such as curvature. For example, if the warp profile of a piece of lumber was described by the function Warp=a+bx+cx$^2$ (0<x<L), then the first differential profile would be given by Warp'=b+2cx (0<x<L) and the second differential profile would be given by Warp"=2c, where L is the length of the board in appropriate units. In general, the warp profile of a lumber product will not be described by an analytic function, and numeric methods will be used to approximate the differential profiles, as is well known in the art. And in practice, differential characteristic profiles will not be constant in x.

Next, in an optional embodiment, the moisture content of the board may be changed. In an embodiment, this may be performed via drying in a kiln. The new warp profile and new moisture content are then recorded, and converted to a new differential characteristic profile.

Next, a prediction model or algorithm is determined using information from the sensor group(s), the original warp-profile data and moisture content, and the information derived from the new moisture content described in the preceding paragraph. The prediction model may be used to 1) predict the differential characteristic of a section of lumber as a function of MC using a set of inputs, or 2) predict curvature-change of a section of lumber using a set of inputs, or 3) predict curvature of a section of lumber at a specific moisture content as a function of inputs. In a next step, the differential characteristic on a given piece of lumber is predicted. This is done by obtaining various data or inputs such as those described above (i.e., sensor group(s) data, warp, moisture content), and inputting the data into the prediction model or algorithm to obtain a differential characteristic prediction. In an additional step, a warp profile may be constructed from one or more differential characteristic predictions on a piece of lumber. This may also require boundary conditions if joining more than one section of a piece of lumber. In another embodiment, the results of the warp profile may be summarized for use in subsequent prediction algorithms. In yet another embodiment, the lumber may be sorted based on the predictions.

Note: If the Cartesian representation of a curve can be considered by the form y=F(x), the curvature K of F can be written as:

$$K = \frac{\left|\frac{d^2 y}{dx^2}\right|}{\left[1+\left(\frac{dy}{dx}\right)^2\right]^{3/2}}.$$

It is also important in our application to know whether the curve is concave or convex as a function of x, so we define the "signed curvature" K* as $$K^* = \frac{\frac{d^2 y}{dx^2}}{\left[1+\left(\frac{dy}{dx}\right)^2\right]^{3/2}}.$$

In most dimensional lumber products, the maximum warp over any section of a piece is small relative to the length of the section. As a result, the denominator in the above equation is nearly always close to 1, and the curvature, K*, of a piece of lumber will be very close to the second derivative.

The present invention may be better understood by the following example.

EXAMPLE 1

This example is taken from a laboratory study of lumber from Idabel, Okla. A sample of 3 units of 2 inch by 4 inch by 8 inch lumber (about 600 boards) was collected from a planer mill in Idabel and sent to Weyerhaeuser Technology Center ("WTC") [Federal Way, Wash.]. This lumber was measured for as-received warp, moisture content and acoustic-velocity at WTC, and then sent to Lucidyne, Inc. for scanning with their GradeScan system, a system for automated visual grading of lumber based on, for example, knots, wane, warp, or the like. The lumber was subsequently allowed to equilibrate in a kiln at 20% relative humidity ("RH"), and then re-measured for warp and moisture content.

The warp measurements made at WTC were taken every inch down the length of the board and the ends of the boards were set to zero displacement. This creates a warp profile. The GradeScan unit measures Red, Green and Blue colors at high-resolution over the board, along with "T1" tracheid information (referring to the projection of light onto a wood surface and observance of the diffusion of light along the surface, outlined in U.S. Pat. No. 3,976,384 issued to Matthews et al. The warp profiles for each board (4 per board—crook and bow, both pre and post equilibration) were converted to second derivative profiles. The second derivative profiles were summarized to obtain the mean second derivative for each one foot segment down the length of each board.

The GradeScan image information was summarized to create "coupon" mean values. Here a coupon represents 1 foot of length of the board, and ¼ of the width for each side of the board. Thus, each 2×4×8 piece of lumber was summarized by 8×2×4=64 coupon means for each channel of information provided by GradeScan. Accordingly, each one foot segment of a piece of lumber had 8 coupons.

Figure 2:
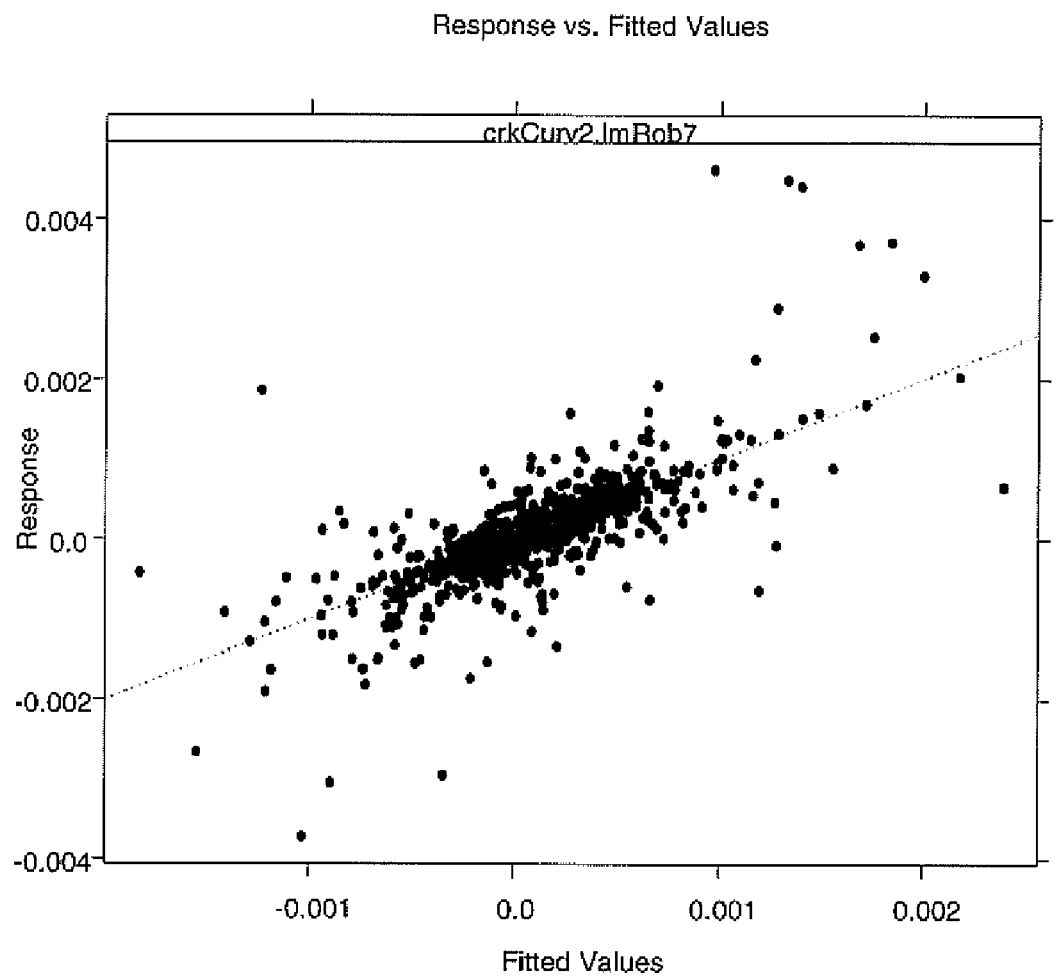
FIG. 2 is a calibration plot in an embodiment of the present invention.

The pre-equilibration moisture content, segment-wise second derivative estimates, and the GradeScan coupon summaries were then used to predict the post-equilibration segment-wise second derivative estimates. This provided a prediction of 20% RH equilibrated second derivative. A calibration plot is shown in FIG. 2.

This second derivative prediction model was then used to predict the segment-wise second derivative of all lumber in the sample. The second derivative values for each board were then double integrated (along with appropriate boundary conditions) to produce a predicted 20% RH profile. An example of a predicted profile is shown in FIG. 3, along with the measured profile.

Figure 4:
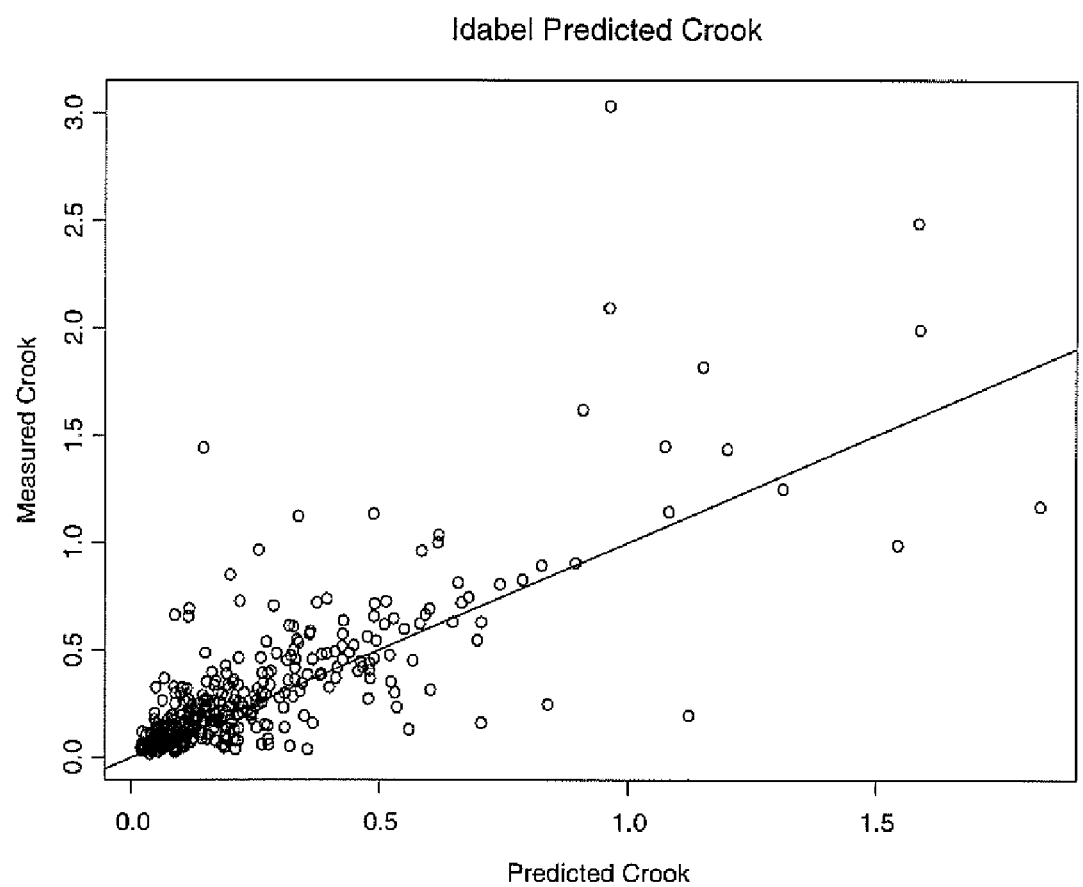
FIG. 4 is a plot of the measured maximum-absolute-displacement (MAD) versus the predicted MAD for a subset of 600 Idabel boards in an embodiment of the present invention.

There are many ways to describe the agreement between the predicted and measured profiles. One method is to compare the maximum-absolute-displacement (MAD), since this is a value that determines the warp grade. A plot of the measured MAD versus the predicted MAD for a subset of the 600 Idabel boards is shown in FIG. 4.

Another optional step (not performed) is to use the predicted MAD, or some other summary of the curvature profile, as an input to a warp prediction algorithm. For example, one might use measurements of acoustic velocity, initial warp, initial moisture content, and the predicted MAD to predict the warp at some end-point moisture content.

The methods for determining warp stability or any of the other properties mentioned above may involve the use of single and/or multiple sensor group systems to provide qualitative and/or quantitative estimates. It has been discovered that estimates of warp/dimensional stability can be much improved when an assortment of measurements are used together, where each measurement contributes information relating to one or more variables. The measurements may be taken at one or more sections of the wood product (i.e., log or board), which may differ in size given a particular embodiment. The properties observed at the one or more sections may allow a qualitative and/or quantitative estimate of dimensional stability of a region of interest. In a first embodiment, the region of interest may be a coupon or other portion of the wood product. In another embodiment, the region of interest may overlap with one or more sections of the wood product. In another embodiment, the region of interest may be the entire wood product. In yet another embodiment, the region of interest may be the same as the one or more sections detected by the sensor group(s). In another embodiment, the region of interest does not have an overlap with the one or more sections. The dimensional stability assessed may be cup, crook, bow, twist, length stability, thickness stability, width stability, or any combination of these.

In an embodiment of the present invention, a classification algorithm may be created to classify a wood product into one of a plurality of groups or categories. The groups may be based on qualitative or quantitative characteristics. For example, in an embodiment, the categories may be different grades. Warp classification of wood products, such as boards may require inputs from one or more sensor groups detecting properties of the boards. The sensor groups may be a part of those systems previously mentioned for analyzing a wood product. The technologies for these systems are known by those skilled in the art. For example, the sensor groups may obtain moisture content measurement, electrical property measurement, structural property measurement, acousto-ultrasonic property measurement, light scatter (tracheid-effect) measurement, grain angle measurement, shape measurement, color measurement, spectral measurement and/or defect maps. Structural property measurement may measure modulus of elasticity, density, specific gravity, strength, or a combination of these. Acousto-ultrasonic property measurement measures may measure velocity and/or damping. The spectral measurement may be characterized by absorption or reflectance values over a wavelength spectrum ranging from ultraviolet through near infrared.

Using this approach, the prediction model or algorithm of the present invention may use inputs of many different resolution scales. Some examples are board average MOE, moisture content measured across the width of the board in one foot increments along the length of the board, spectroscopy data collected every inch, or laser data collected every ¼ inch.

The inputs are functions of the sensor signals and may be either quantitative or qualitative. For example, an input could be the estimated moisture content for each 12 inch lineal section of a piece of lumber, as estimated by a moisture meter. Another example is an indicator for the presence or absence of a knot in a 12 inch by 1 inch section of wood, based on a color image. Inputs may be direct sensor measurements, pre-processed signals, combined signals from several sensors or predicted measures from other sensors. Signal pre-processing may include, but is not limited to, such steps as filtering, smoothing, derivative calculations, power spectrum calculations, Fourier transforms, etc., as is well known in the art. Predicted measurements from other sensors may include, but are not limited to, shrinkage-coefficients predicted from sensors which measure the light scattering and light absorption properties of wood and used as inputs to a partial least squares, or "PLS", prediction model.

The prediction algorithm(s) or model(s) based on the set of inputs can be derived using many techniques which include, but are not limited to, regression trees, classification trees, linear discriminant analysis, quadratic discriminant analysis, logistic regression, Partial Least Squares or other supervised learning techniques such as neural networks. There are many forms of equations or algorithms that could be used, and a general reference is Hastie, et al[3].

[3]Hastie, T., Tibshirani, R., and Friedman, J., (2001) The Elements of Statistical Learning, Springer, N.Y.

These algorithms can be developed to classify boards into 2 or more groups. For example, boards might be classified into four grades (#1 grade, #2 grade, #3 grade, #4 grade) or into two classifications like warp stable and warp unstable, or into three categories like crook less than 0.25 inches, crook between 0.25 and 0.5 inches, crook greater than 0.5 inches. Typically, the parameters in the models or algorithms are derived from a training-set of data and the performance is tested on a testing-set of data before being used in production, although other approaches exist.

Various embodiments are contemplated involving the use of sensor groups and algorithms. In a first embodiment, a single sensor group may provide inputs to a classification algorithm which classifies wood products into one of a plurality of groups or categories, such as grades, for example.

In a second embodiment, a single sensor group may provide inputs to a classification algorithm as in the previous example. However, in this embodiment, a second algorithm may be selected after classifying the wood product. This second algorithm may be selected from a plurality of algorithms which are used to assess the dimensional stability in a quantitative manner.

In a third embodiment, two or more sensor groups may provide two or more inputs to a classification algorithm to classify wood products into one of a plurality of categories.

In a fourth embodiment, two or more sensor groups may provide two or more inputs to an algorithm for providing a quantitative assessment of dimensional stability of wood products.

In a fifth embodiment, two or more sensor groups may provide two or more inputs to a classification algorithm to classify wood products into one of a plurality of categories. Next, a second algorithm may be selected after classifying the wood product. This second algorithm may be selected from a plurality of algorithms which are used to assess the dimensional stability in a quantitative manner.

Other methods for determining warp stability, wane, moisture, knot properties, or the like for a log or board are contemplated, including those described in U.S. Pat. Nos. 6,308,571; 6,305,224; and 6,293,152 to Stanish et al., or any other known methods currently used at mill sites. These methods could be implemented into the process steps described above.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for predicting warp of a given wood product, the method comprising the steps of:
   measuring at least one original warp profile for each of one or more first wood products;
   measuring one or more inputs on the one or more first wood products;
   converting the warp profile, for each of the one or more first wood products, into a differential characteristic profile;
   developing a prediction algorithm based on the one or more inputs and the differential characteristic profile;
   measuring one or more inputs of the given wood product;
   inputting the one or more inputs of the given wood product into the prediction algorithm; and
   determining a differential characteristic profile for the given wood product based on the prediction algorithm.

2. The method of claim 1, further comprising the step of: integrating the differential characteristic profile to obtain a warp profile.

3. The method of claim 2, wherein the at least one warp profile is based on crook.

4. The method of claim 2, wherein the at least one warp profile is based on bow.

5. The method of claim 2, wherein the at least one warp profile is based on twist.

6. The method of claim 2, wherein the at least one warp profile is based on cup.

7. The method of claim 1, wherein the input is based on at least one of moisture content measurement, electrical property measurement, structural property measurement, acousto-ultrasonic property measurement, light scatter (tracheid-effect) measurement, grain angle measurement, shape measurement, color measurement, spectral measurement and/or defect maps.

8. The method of claim 7, wherein structural property measurement includes measuring at least one of: modulus of elasticity, density, specific gravity, and strength.

9. The method of claim 1, wherein the characteristic is at least one of: first derivative, second derivative, and curvature.

10. The method of claim 1, wherein the prediction algorithm is based on at least one of: regression trees, classification trees, linear discriminant analysis, quadratic discriminant analysis, logistic regression, Partial Least Squares and neural networks, linear regression, generalized linear regression, non-linear regression, generalized additive regression, projection pursuit regression, or look-up tables.

11. The method of claim 1, wherein the warp profile for the first wood product is determined based on measurements taken at one or more sections of the wood product.

12. The method of claim 1, wherein the differential characteristic profile represents a differential of the warp profile.

13. The method of claim 1, wherein the differential characteristic profile is selected from the group consisting of the warp profile's first derivative, the warp profile's second derivative, and the warp profile's curvature.

* * * * *